United States Patent
Kennedy et al.

(10) Patent No.: US 10,478,466 B1
(45) Date of Patent: Nov. 19, 2019

(54) TOPICAL VASODILATOR COMPOSITION

(71) Applicants: Peter Kennedy, Pacific Palisades, CA (US); Carolyn Shawn Murphy, Harrison, OH (US)

(72) Inventors: Peter Kennedy, Pacific Palisades, CA (US); Carolyn Shawn Murphy, Harrison, OH (US)

( * ) Notice: Subject to any disclaimer, the term of this patent is extended or adjusted under 35 U.S.C. 154(b) by 0 days.

(21) Appl. No.: 16/158,363

(22) Filed: Oct. 12, 2018

Related U.S. Application Data

(63) Continuation-in-part of application No. 15/043,940, filed on Feb. 15, 2016.

(60) Provisional application No. 62/116,152, filed on Feb. 13, 2015.

(51) Int. Cl.

| | | |
|---|---|---|
| *A61K 36/258* | (2006.01) | |
| *A61K 9/06* | (2006.01) | |
| *A61K 9/00* | (2006.01) | |
| *A61K 47/44* | (2017.01) | |
| *A61P 9/08* | (2006.01) | |
| *A61K 47/10* | (2017.01) | |
| *A61K 47/22* | (2006.01) | |
| *A61K 47/18* | (2017.01) | |
| *A61K 47/34* | (2017.01) | |

(52) U.S. Cl.
CPC .......... *A61K 36/258* (2013.01); *A61K 9/0014* (2013.01); *A61K 9/06* (2013.01); *A61K 47/10* (2013.01); *A61K 47/18* (2013.01); *A61K 47/22* (2013.01); *A61K 47/34* (2013.01); *A61K 47/44* (2013.01); *A61P 9/08* (2018.01)

(58) Field of Classification Search
None
See application file for complete search history.

(56) References Cited

U.S. PATENT DOCUMENTS

| | | |
|---|---|---|
| 5,874,479 A | 2/1999 | Martin |
| 5,902,600 A | 5/1999 | Woller et al. |
| 5,916,573 A | 6/1999 | Spiers et al. |
| 6,579,543 B1 | 6/2003 | McClung |
| 6,630,163 B1 | 10/2003 | Murad |
| 8,673,278 B2 | 3/2014 | Cranner et al. |
| 2003/0232091 A1 | 12/2003 | Shefer et al. |
| 2010/0087546 A1 | 4/2010 | Appleton |
| 2010/0124549 A1 | 5/2010 | Studin |
| 2011/0135627 A1 | 6/2011 | LaMotta et al. |
| 2011/0305643 A1 | 12/2011 | Gurge et al. |
| 2013/0058885 A1 | 3/2013 | Burt et al. |
| 2014/0248224 A1 | 9/2014 | Vaidya et al. |
| 2014/0255526 A1 | 9/2014 | Shan et al. |

FOREIGN PATENT DOCUMENTS

| | | |
|---|---|---|
| CA | 2620242 | 9/2009 |
| CN | 103735488 | 4/2014 |
| WO | 2013149323 | 10/2013 |
| WO | 2013178758 | 12/2013 |
| WO | 2014184315 | 11/2014 |

OTHER PUBLICATIONS

Dow Corning 9546 Silicone Elastomer Blend, Apr. 2009 (Dow Corning), p. 1, composition.
PCT International Search Report; dated Apr. 29, 2016; PCT International Application No. PCT/US2016/017975; filed Feb. 15, 2016; Applicant: Peter Kennedy, et al.; pp. 1-11.

*Primary Examiner* — Nannette Holloman
(74) *Attorney, Agent, or Firm* — Hall Estill Law Firm

(57) ABSTRACT

A topical composition comprising from about 0.05% to about 10.0% by weight of Arnica oil, from about 5.0% to about 20.0% by weight of a notoginseng herb comprising dammarane-type ginsenosides, from about 0.05% to about 10% by weight of a compound comprising cyclopentasiloxane, dimethicone crosspolymer, dimethicone/vinyl dimethicone crosspolymer, dimethiconol, and a cosmetically acceptable aqueous carrier.

13 Claims, No Drawings

TOPICAL VASODILATOR COMPOSITION

RELATED APPLICATIONS

This application is a continuation-in-part of U.S. patent application Ser. No. 15/043,940, filed on Feb. 15, 2016 which in turn claims priority to U.S. Provisional Patent Application No. 62/116,152 filed Feb. 13, 2015, the contents of which are hereby incorporated by reference.

FIELD OF THE INVENTION

The present invention relates to a topical skin treatment composition for the treatment of bruises.

BACKGROUND

A bruise, also known as a contusion, is a common skin injury that results from the breakage of tiny blood vessels leaking under the skin. Blood from damaged blood vessels beneath the skin collects near the surface of the skin to appear as what we recognize as a black and blue mark. This mark is from skin discoloration by red blood cells and their contents. Generally, there are limited treatments for contusions to the skin. Vascular dilators may be administered in an amount sufficient to improve blood supply to the skin. Without wishing to be bound by theory, vascular dilators are also believed to strengthen blood vessels. Bruise creams generally are available to consumers, which typically include at least Arnica oil either alone or in combination with Witch Hazel or Menthol. However, there is little evidence found that Arnica containing products actually reduce the duration of contusions. See Alonso D., Lazarus M. C., Baumann L; "Effects of topical arnica gel on post-laser treatment bruises" *Dermatol Surg.* 2002 Aug. 28(8): 686-8.

A need continues to exist for a treatment that reduces the duration of contusions of the skin.

SUMMARY OF THE INVENTION

The present invention is directed to a topical composition comprising from about 0.05% to about 10.0% by weight of Arnica oil, from about 5.0% to about 20.0% by weight of a Panax herb comprising dammarane-type ginsenoside, and a cosmetically acceptable aqueous carrier.

DETAILED DESCRIPTION

The topical composition of the present invention comprises from about 0.05% to about 10.0% of Arnica oil. The composition also comprises from about 5.0% to about 20.0% of a Panax herb comprising dammarane-type ginsenoside. The topical composition is available in a cosmetically acceptable aqueous carrier.

The topical composition of the present invention comprises from about 0.05% to about 10.0%, preferably from about 0.5% to about 8%, more preferably from about 1.0% to about 5.0% by weight of the composition of Arnica oil. Arnica Oil or *Arnica montana* extract is a species containing helenalin, which is a sesquiterpene lactone possessing anti-inflammatory properties especially beneficial against bruising. *Arnica montana* extract stimulates activity of white blood cells, thus causing reduction of bruising and swelling. It assists the healing process by facilitating transport of blood and fluid accumulated in the injured area through a dilating action of subcutaneous blood capillaries. It accelerates the healing of damaged tissues by encouraging immune cell function and shortens the recovery time after the surgery or injury.

The topical composition of the present invention also comprises from about 5.0% to about 25.0%, preferably from about 8% to about 12%, more preferably from about 6.0% to about 10%, by weight of the composition of a Panax herb comprising dammarane-type ginsenosides. In preferred embodiments of the topical composition of the present invention the Panax herb comprising dammarane-type ginsenosides is selected from the group consisting of *Panax ginseng, Panax quinquefolius, Panax vietnamensis,* and *Panax notoginseng* and mixtures thereof. In a more preferable embodiment of the topical composition the Panax herb comprises *Panax notoginseng*.

In an alternate embodiment, the topical composition of the present invention also comprises from about 20.0% to about 30.0%, preferably from about 22.0% to about 28.0%, more preferably from about 24.0% to about 26.0%, by weight of the composition of a Panax herb comprising dammarane-type ginsenosides. In preferred embodiments of the topical composition of the present invention the Panax herb comprising dammarane-type ginsenosides is selected from the group consisting of *Panax ginseng, Panax quinquefolius, Panax vietnamensis,* and *Panax notoginseng* and mixtures thereof. In a more preferable embodiment of the topical composition the Panax herb comprises *Panax notoginseng*.

Panax ginsenosides are hemostatic perennial herbs predominantly grown in China and Japan and are known for their ability to invigorate the body and build blood. They are often used for treatment of blood related diseases and conditions, including blood stasis, angina, coronary heart disease. They are used to treat adrenal glands and conditions related to make sex hormones and prostate cancer.

A Panax ginsenoside composition may be produced by the process described in U.S. Pat. No. 6,500,468 B1, issued to Zeng et al. on Dec. 31, 2002.

The topical composition of the present invention further comprises a cosmetically acceptable aqueous carrier. The carrier comprises from about 70% to about 99.45% by weight of the composition. The carrier may be in the form of an ointment, cream, lotion, gel, paste, solution, or other such carriers known in the art. The carrier may contain liposomes, micelles, and/or microspheres. Carriers useful in this invention include any such materials known in the art that are nontoxic and do not interact with other components of the composition in a deleterious manner.

A preferred embodiment of the topical composition of the present invention comprises a carrier that is an ointment. Ointments, as is well known in the art, are semisolid preparations based on petrolatum or petrolatum derivatives. The specific ointment base to be used is one that will provide for optimum delivery of the composition and will provide other desirable characteristics, for example emoliency. Ointment bases may also contain vegetable oils, fats obtained from animals or polyethylene glycols.

Another preferred embodiment of the topical composition comprises a carrier that is a cream. Creams are viscous liquids or semisolid emulsions, either oil-in-water or water-in-oil. Cream bases contain an oil phase, an emulsifier, and an aqueous phase. The oil phase generally comprises petrolatum and a fatty alcohol such as cetyl or stearyl alcohol. The aqueous phase usually exceeds the oil phase in volume and may contain a humectant. The emulsifier is generally a nonionic, anionic, cationic or amphoteric surfactant.

Another preferred embodiment of the topical composition comprises a carrier that is a gel. Gels are semi-solid suspension-type systems. Single-phase gels contain organic macromolecules distributed substantially uniformly throughout the carrier liquid, which is typically aqueous, but also, preferably, contains an alcohol and, optionally, an oil. Preferred gelling agents are crosslinked acrylic acid polymers, such as the "carbomer" family of polymers. E.g. carboxypolyalkylenes. Also preferred are hydrophilic polymers such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose and methylcellulose; gums such as tragacanth and xanthan gum, sodium alginate; and gelatin. In order to prepare a uniform gel, dispersing agents such as alcohol or glycerin can be added, or the gelling agent can be dispersed by trituration, mechanical mixing, or stirring, or combination thereof.

Another preferred embodiment of the topical composition comprises a carrier that is a lotion. Lotions are preparations to be applied to the skin surface without friction and are typically liquid or semiliquid preparation in which solid particles, including the active agents are present in a water or alcohol base. Lotions are usually suspensions of solids and preferably comprise a liquid oily emulsion of the oil-in-water type. It is generally necessary that the insoluble matter in a lotion be finely divided. Lotions typically contain suspending agents to produce better dispersion as well as compounds useful for localizing and holding the active agent in contact with the skin, e.g., methylcellulose, sodium carboxymethylcellulose, or the like.

An additional preferred embodiment of the topical composition of the present invention comprises a carrier that is a paste. Pastes are semisolid dosage forms in which the active agent is suspended in a suitable base. Depending on the nature of the base, pastes are divided between fatty pastes or those made from a single-phase aqueous gels. The base in a fatty paste is generally petrolatum, hydrophilic petrolatum, or the like. The pastes made from single-phase aqueous gels generally incorporate carboxymethylcellulose or the like as a base.

Formulations for the topical compositions may also be prepared with liposomes, micelles, and microspheres. Liposomes are microscopic vesicles having a lipid wall comprising a lipid bilayer, and can be used for topical delivery of the present composition as well. Liposomal preparations for use in this invention include cationic, anionic and neutral preparations.

Micelles are known as comprised of surfactant molecules arranged so that their polar headgroups form an outer spherical shell, while their hydrophobic hydrocarbon chains are oriented towards the center of the sphere forming a core. Micelles form in aqueous solution containing surfactant at a high enough concentration so that micelles naturally result. Surfactants useful for forming micelles include, but are not limited to, potassium laurate, sodium octane sulfonate, sodium decane sulfonate, sodium lauryl sulfate, docusate sodium, decyltrimethylammonium bromide, dodecyltrimethylammonium bromide, tetradecyltrimethylammonium bromide, dodecyl ammonium chloride, polyoxyl 12 dodecyl ether, and nonoxynol 30. Micelle formulations can be used in conjunction with the present invention either by incorporation into the reservoir of a topical delivery system, or into a formulation to be applied to the body surface.

Microspheres may also be used for topical administration of the composition of the present invention. Similarly, like liposomes and micelles, microspheres essentially encapsulate a composition to be applied on the skin. Microspheres are generally formed from synthetic or naturally occurring biocompatible polymers, but may also be comprised of charged lipids such as phospholipids.

The carrier in any form of topical delivery should be biologically and chemically inert, non-toxic, non-irritating and not interacting with components of the composition. Additionally, a carrier should provide for deep penetration of the composition into the skin.

The topical composition of this invention is a homeopathic composition comprising naturally derived ingredients, which can be used safely at the same time as conventional medicines, promoting accelerated time of recovery after surgery or skin injury, and guarding against staining of skin, swelling and pain.

Methods of Use—The topical composition of the present invention are preferably applied topically to the desired area of the skin in an amount sufficient to provide effective delivery of the Arnica oil and Panax ginsenoside.

Method of Manufacture—The topical compositions of the present invention may be prepared by any known or otherwise effective techniques, suitable for making the desired composition.

EXAMPLE

The following example further describes and demonstrates the embodiments of the present invention within the scope of the invention. The example is given solely for the purpose of illustration and is not to be considered as limitations of the present invention, as many variations thereof are possible without departing from the spirit and scope of the invention. All exemplified amounts are concentrations by weight of the Each exemplified example promotes improved healing and dissipation of contusions of the skin, as measured by the discoloration of the skin at the site of the contusion, through at least vasodilatation of the region afflicted by the contusion, when the composition is topical applied to the region of the skin presenting the contusion.

Example 1

| | |
|---|---|
| Water | 71.42% |
| Glycerin | 3.00% |
| Arnica Oil | 2.00% |
| Potassium Cetyl Phosphate | 0.75% |
| Glyceryl Stearate Citrate | 3.00% |
| Caprylic/Capric Triglyderides | 4.25% |
| Shea Butter | 2.00% |
| Ceteareth 20 | 2.00% |
| Cetearyl Alcohol | 4.17% |
| *Panax Notoginseng* | 5.00% |
| MSM | 0.75% |
| Dimethicone 200 Fluid | 0.50% |
| Phytonadione (Vitamin K) | 0.25% |
| *Camellia Sinensis* (Green Tea) Leaf Extract | 0.01% |
| Vitamin E | 0.10% |
| Germall | 0.80% |

Example 2

| | |
|---|---|
| Water | 58.35% |
| Glycerin | 2.60% |

-continued

| | |
|---|---|
| Arnica Oil | 1.72% |
| Potassium Cetyl Phosphate | 0.65% |
| Glyceryl Stearate Citrate | 2.60% |
| Caprylic/Capric Triglyderides | 3.65% |
| Shea Butter | 1.72% |
| Ceteareth 20 | 1.72% |
| Cetearyl Alcohol | 3.58% |
| *Panax Notoginseng* | 21.00% |
| MSM | 0.75% |
| Dimethicone 200 Fluid | 0.50% |
| Phytonadione (Vitamin K) | 0.25% |
| *Camellia Sinensis* (Green Tea) Leaf Extract | 0.01% |
| Vitamin E | 0.10% |
| Germall | 0.80% |

Example 3

| | |
|---|---|
| Water (or) Aqua | 60.44% |
| Dimethyl Sulfone | 1.50% |
| Carbomer | 0.50% |
| Caprylic/Capric Triglycerides | 2.50% |
| Glyceryl Stearate Citrate | 3.00% |
| *Arnica Montana* Flower Oil | 7.00% |
| Cetearyl Alcohol | 3.25% |
| Glyceryl Stearate (and) PEG 100 Stearate | 1.50% |
| Glyceryl Stearate (and) Behenyl Alcohol (and) Palmitic Acid (and) Stearic Acid (and) Lecithin (and) Lauryl Alcohol (and) Myristyl Alcohol (and) Cetyl Alcohol | 0.50% |
| *Butyrospermum Parkii* (Shea Butter) | 0.10% |
| Dimethicone | 4.00% |
| Cyclopentasiloxane | 1.50% |
| Cyclopentasiloxane (and) Dimethicone Crosspolymer (and) Dimethicone/Vinyl Dimethicone Crosspolymer (and) Dimethiconol | 7.00% |
| Notoginseng Powder | 5.00% |
| Phytonadione (Vitamin K1) | 0.25% |
| *Camellia Sinensis* (Green Tea) Leaf Extract | 0.01% |
| Tocopheryl Acetate | 0.10% |
| Potassium Hydroxide | 0.35% |
| Hydroxyacetophenone | 0.50% |
| 1,2-Hexanediol (and) Caprylyl Glycol | 1.00% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical composition comprising:
   (a) from about 0.05% to about 10.0% by weight of Arnica oil;
   (b) from about 5.0% to about 20.0% by weight of a notoginseng herb comprising dammarane-type ginsenosides;
   (c) from about 0.05% to about 10% by weight of a compound comprising cyclopentasiloxane, dimethicone crosspolymer, dimethicone/vinyl dimethicone crosspolymer, and dimethiconol;
   (d) from about 0.05% to about 5.0% by weight cetearyl alcohol;
   (e) from about 0.75% to about 0.85% by weight of a compound formed from diazolidinyl urea ("DU") and iodopropynyl butylcarbamate ("IPBC"), wherein the ratio of DU to IPBC is substantially 99% to 1% by weight;
   (f) about 0.05% to about 2.5% by weight of dimethyl sulfone;
   (g) about 0.25% weight of phytonadione; and
   a cosmetically acceptable aqueous carrier, wherein upon a topical application of the composition to a skin contusion region, such application promotes vasodilatation in the region and dissipation of the contusion, wherein the notoginseng herb comprising dammarane-type ginsenosides is selected from the group consisting of, *Panax quinquefolius, Panax vietnamensis*, and *Panax notoginseng* and mixtures thereof.

2. The topical composition according to claim 1, in which the cetearyl alcohol comprising from about 1.05% to about 4.0% by weight cetearyl alcohol.

3. The topical composition according to claim 1, further comprising from about 0.05% to about 8.0% by weight dimethicone.

4. The topical composition according to claim 3, further comprising from about 0.01% to about 2.5% by weight of cyclopentasiloxane.

5. The topical composition according to claim 1, further comprising from about 0.01% to about 2.5% by weight of cyclopentasiloxane.

6. The topical composition according to claim 5, further comprising from about 2.75% to about 3.25% by weight of glycerin.

7. The topical composition according to claim 1, further comprising about 0.10% by weight of vitamin E.

8. The topical composition according to claim 1, in which the cosmetically acceptable aqueous carrier is in the form of an ointment.

9. The topical composition according to claim 1, in which the cosmetically acceptable aqueous carrier is in the form of a cream.

10. The topical composition according to claim 1, in which the cosmetically acceptable aqueous carrier is in the form of a gel.

11. The topical composition according to claim 1, in which the cosmetically acceptable aqueous carrier is in the form of a lotion.

12. The topical composition according to claim 1, in which the cosmetically acceptable aqueous carrier is in the form of a paste.

13. The topical composition according to claim 1, further comprising liposomes, and/or micelles, and/or microspheres, wherein the liposomal preparation include cationic, and/or anionic, and/or neutral preparations.

* * * * *